United States Patent [19]
Sugimoto et al.

[11] Patent Number: 5,237,403
[45] Date of Patent: Aug. 17, 1993

[54] LIGHT SOURCE SYSTEM FOR ENDOSCOPE

[75] Inventors: Hideo Sugimoto; Rensuke Adachi, both of Tokyo, Japan

[73] Assignee: Asahi Kogaku Kogyo Kabushiki Kaisha, Tokyo, Japan

[21] Appl. No.: 752,214

[22] Filed: Aug. 21, 1991

Related U.S. Application Data

[63] Continuation of Ser. No. 564,703, Aug. 7, 1990, which is a continuation of Ser. No. 301,588, Jan. 26, 1989.

[30] Foreign Application Priority Data

Feb. 4, 1988 [JP] Japan .................................. 63-25426

[51] Int. Cl.⁵ ........................... H04N 7/18; A61B 1/06
[52] U.S. Cl. ............................................ 358/98; 128/6
[58] Field of Search .............. 358/98; 128/6; 359/227, 359/232, 235, 236

[56] References Cited

U.S. PATENT DOCUMENTS

| | | | |
|---|---|---|---|
| 4,834,071 | 5/1989 | Hosoi et al. | 358/98 |
| 4,868,645 | 9/1989 | Kobayashi | 358/98 |
| 5,042,915 | 8/1991 | Akutsu et al. | 358/98 |

FOREIGN PATENT DOCUMENTS

| | | |
|---|---|---|
| 3526993 | 9/1987 | Fed. Rep. of Germany . |
| 61-37226 | 2/1986 | Japan . |
| 61-175609 | 8/1986 | Japan . |
| 63-182621 | 7/1988 | Japan . |

Primary Examiner—Edward L. Coles, Sr.
Assistant Examiner—Thomas D. Lee
Attorney, Agent, or Firm—Sandler Greenblum & Bernstein

[57] ABSTRACT

A condenser lens is provided between a light source and the incident end of an illumination light guide, and at least one pair of plane-parallel plates are disposed on the illumination light path at a position between the light source and the condenser lens in such a manner that the plates are in symmetry with each other with respect to the optical axis of the illumination light path. The plane-parallel plates are pivoted by a pivoting device about an axis of rotation which extends perpendicular to the optical axis of illumination light and parallel with the plane-parallel plates, thereby partially intercepting the illumination light path, and thus adjusting the quantity of light which is applied from the light source to the illumination light guide.

13 Claims, 4 Drawing Sheets

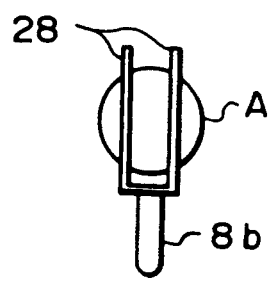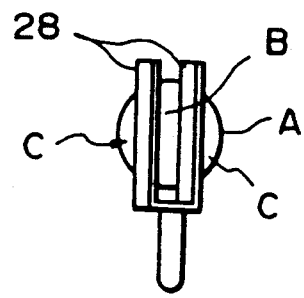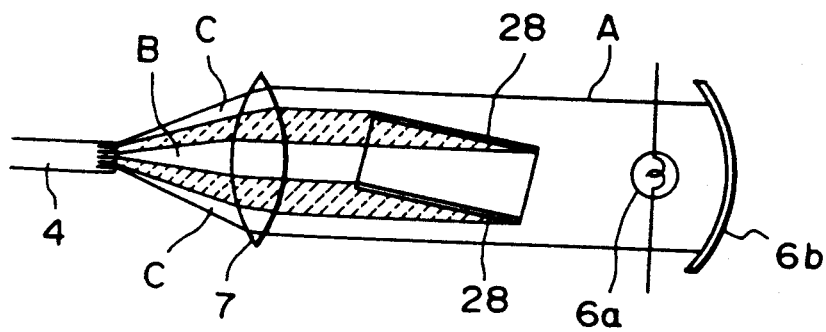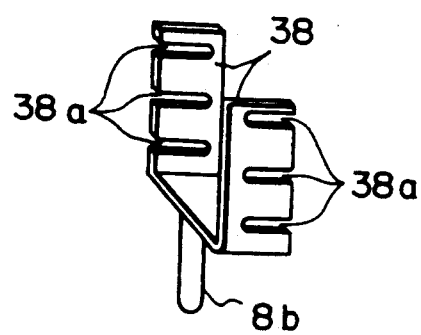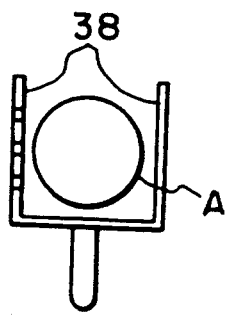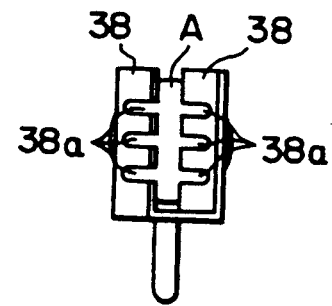

LIGHT SOURCE SYSTEM FOR ENDOSCOPE

This application is a continuation of application Ser. No. 07/564,703, filed Aug. 7, 1990, now abandoned; which is a continuation of application Ser. No. 07/301,588 filed Jan. 26, 1989.

BACKGROUND OF THE INVENTION

1. Field of the Invention

The present invention relates to a light source system for an endoscope. More particularly, the present invention pertains to a light source system for an endoscope which is designed so that it is possible to adjust the quantity of illumination light which is applied to the incident end of a light guide from a light source.

2. Description of the Related Art

The type of light source system for an endoscope is generally arranged such that illumination light which is emitted from a light source lamp is formed into parallel rays by means of a reflecting mirror and these parallel rays converge through a condenser lens so as to enter the incident end of an illumination light guide. A movable light-shielding plate which partially intercepts the illumination light is provided at an intermediate position along the path of the illumination light which travels from the light source lamp toward the incident end of the light guide. The light-shielding plate can be sidewardly advanced into and withdrawn from the illumination light path, and the position of the movable light-shielding plate is automatically controlled to adjust the quantity of illumination light.

The above-described prior art suffers, however, from the following problems. Since the illumination light is partially intercepted by means of the movable light-shielding plate which is sidewardly advanced into the illumination light path, as the quantity of illumination light is decreased, the cross-sectional area of the illumination light path gradually narrows down and eventually only the illumination light which passes through the peripheral portion of the illumination light path enters the light guide. Since the illumination light is refracted to a substantial degree at the peripheral portion of the lens, the optical paths of components of the refracted light diverge from each other in accordance with the wavelength of each light component, which results in a change in the spectral characteristics of the illumination light entering the light guide. As a result, no precise color reproduction is available for an observed image on a monitor screen. Further, since in the prior art, a delay in the response of the movable light-shielding plate is present, the brightness of the observed image on the monitor screen cannot be maintained at a constant level.

SUMMARY OF THE INVENTION

An object of the present invention is to provide a light source system for an endoscope which is designed so that a change in the quantity of illumination light which is incident on a light guide causes a minimized change in the spectral characteristics of the incident light.

Other objects and advantages of the present invention will become apparent from the following detailed description of illustrated embodiments of the invention.

According to the present invention, there is provided a light source system for an endoscope designed to supply illumination light to an illumination light guide of the endoscope, comprising: a light source which emits illumination light; a condenser lens for converging the illumination light emitted from the light source on the incident end of the illumination light guide; at least one pair of plane-parallel plates disposed in the illumination light path at a position between the light source and the condenser lens in such a manner that the plates are in symmetry with each other with respect to the optical axis of the illumination light path; and a device for pivoting the plane-parallel plates about an axis of rotation which extends perpendicular to the optical axis of the illumination light and parallel with the plane-parallel plates, whereby the plane-parallel plates are pivoted by the pivoting device so as to partially intercept the illumination light path, thereby adjusting the quantity of light entering the illumination light guide.

BRIEF DESCRIPTION OF THE DRAWINGS

The present invention may be more fully understood from the description of preferred embodiments of the invention set forth below, together with the accompanying drawings, in which:

FIG. 6 is a side view of the illumination light path in a second embodiment of the present invention;

FIG. 7 is a side view of the illumination light path where plane-parallel plates according to the second embodiment are in a pivoted position;

FIG. 8 is a plan view of the illumination light path shown in FIG. 7;

FIG. 9 is a perspective view of plane-parallel plates according to a third embodiment of the present invention;

FIG. 10 is a side view of the plane-parallel plates according to the third embodiment;

FIG. 11 is a side view of the plane-parallel plates according to the third embodiment which are in a pivoted position;

DESCRIPTION OF THE EMBODIMENTS

Embodiments of the present invention will be described hereinunder in detail with reference to the accompanying drawings.

Figure 1:
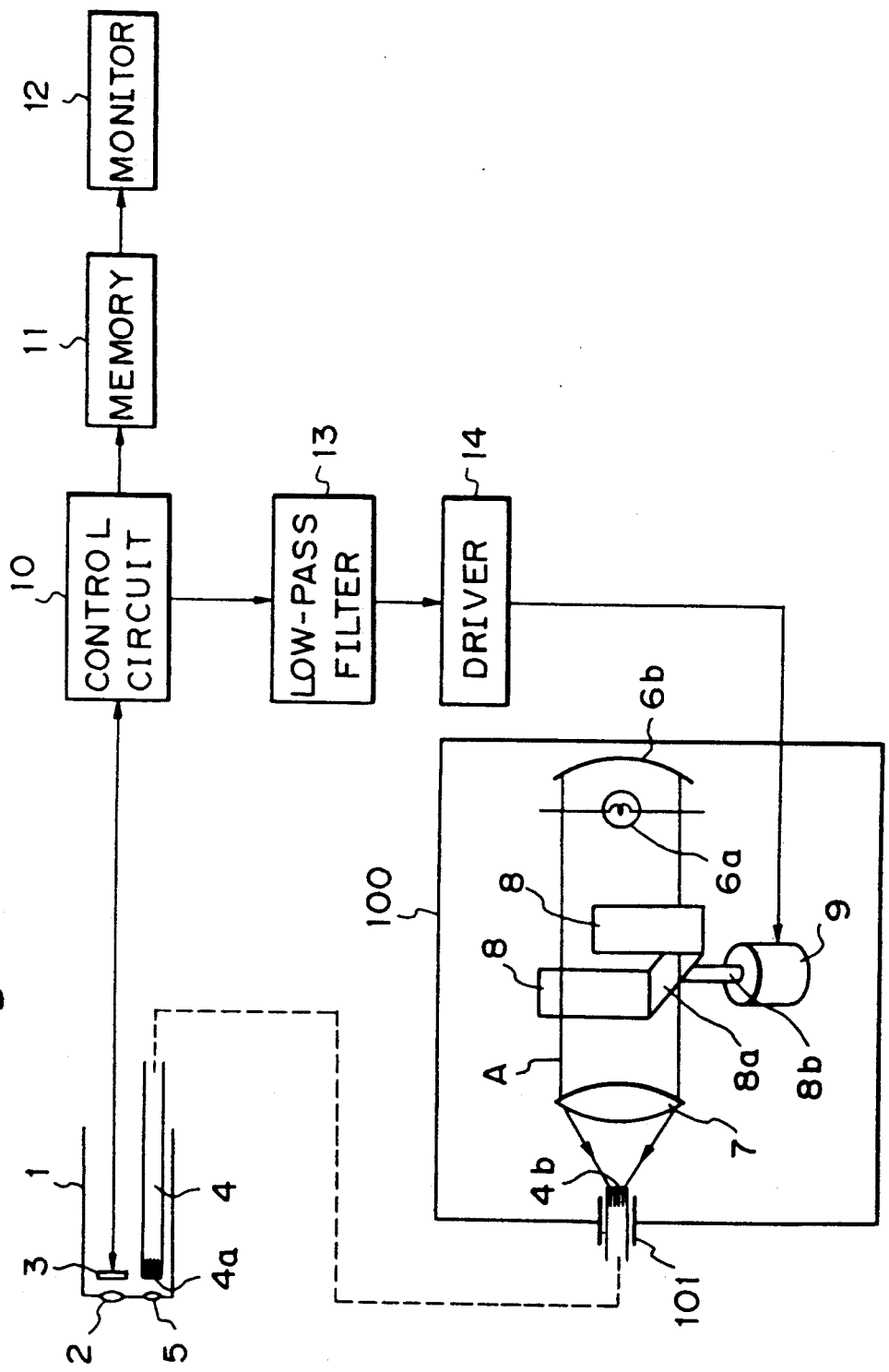
FIG. 1 is a block diagram showing the general arrangement of a first embodiment of the present invention.

Referring first to FIG. 1, the reference numeral 1 denotes an insert part of an endoscope. The reference numeral 2 denotes an objective lens which is disposed at the distal end of the insert part 1. The image receiving surface of a solid-state image pickup device 3 which is defined by, for example, a CCD (Charge-Coupled Device), is disposed at the position where the image of an object of examination is formed by the objective lens 2. The reference numeral 4 denotes a light guide for light that illuminates the range of the visual field of the objective lens 2. The reference numeral 4a denotes the emergent end of the light guide 4. The reference numeral 5 denotes a light distribution lens for enlarging the angle of distribution of the illumination light emitted from the emergent end 4a of the light guide 4. Thus, the image of an object of examination which is illuminated with the light emerging from the illumination light guide 4, that is, the observed image, is converted into an electric signal in the solid-state image pickup device 3. Accordingly, a level of the brightness of the observed image can readily be detected in the form of an electric signal.

A housing 100 for the light source system is provided with a socket 101 into which is detachably inserted the incident end portion 4b of the illumination light guide 4. The reference numeral 6a denotes a light source which is disposed within the housing 100, the light source 6a being defined by, for example, a xenon lamp or a halogen lamp. The reference numeral 6b denotes a reflecting mirror for the light source 6a. The arrangement is such that illumination light which is emitted from the light source 6a is formed into parallel rays by means of the reflecting mirror 6b and these parallel rays are condensed through a condenser lens 7 so as to enter the incident end 4b of the illumination light guide 4. Between the light source 6a and the condenser lens are disposed a pair of plane-parallel plates 8 which are used to adjust the quantity of light that reaches the condenser lens 7. The plane-parallel plates 8 are opaque metal plates, and the movement thereof is controlled by means of a motor 9.

In addition, known color compensating filters (not shown) for the three primary colors are provided at a position along the illumination light path in such a manner that the filters alternately enter the illumination light path at a speed of about 10 to 30 cycles per second. In this way, illumination is effected for the three primary colors in a time-division manner.

The reference numeral 10 denotes a known image signal control circuit which outputs a control signal to the solid-state image pickup device 3 and also processes a signal output from the image pickup device 3. A memory 11 for storing the image signal processed in the control circuit 10 is connected to the output end of the control circuit 10, and a monitor 12 for reproducing an observed image is connected to the output end of the memory 11. The luminance signal output end of the image signal control circuit 10 is connected through a low-pass filter 13 to a driver 14 for driving the motor 9. Accordingly, a luminance signal, that is, a voltage corresponding to a level of brightness of the observed image, which is output from the image signal control circuit 10 is smoothed through the low-pass filter 13, and the motor 9 is driven on the basis of the smoothed luminance signal to control the direction of the plane-parallel plates 8 so that the quantity of light that enters the solid-state image pickup device 3 is maintained at a constant level. Thus, since the motor 9 is driven on the basis of the output signal from the solid-state image pickup device 3 so as to adjust the quantity of illumination light, the brightness of the observed image can be accurately controlled at a constant level. Since the circuit configuration of the control system that is employed for this purpose is known and not directly related to the subject of the present invention, detailed description thereof is omitted.

The pair of plane-parallel plates 8 are formed in the shape of rectangular members having the same size, the plates 8 being formed integral with each other through a connecting plate 8a so as to define a U-shaped configuration as a whole. Accordingly, the illumination light is partially intercepted by the plane-parallel plates 8 bi-symmetrically and uniformly. A rotating shaft 8b is rigidly secured to the center of the bottom of the connecting plate 8a in such a manner that the shaft 8b extends perpendicular to the optical axis of the illumination light and parallel with the plane-parallel plates 8. The other end of the rotating shaft 8b is connected to the motor 9. Thus, as the motor 9 rotates, the plane parallel plates 8 pivot with the rotating shaft 8b.

Figure 2:
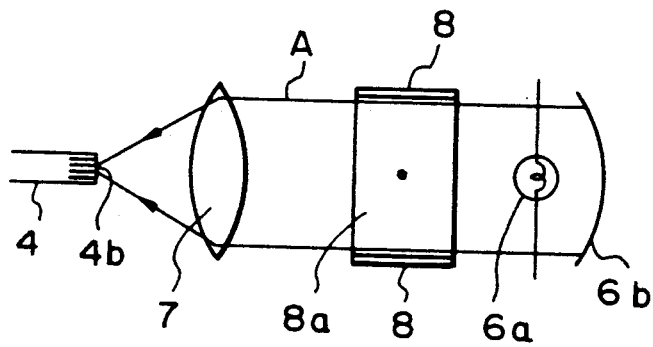
FIG. 2 is a plan view of the illumination light path in the first embodiment.
Figure 3:
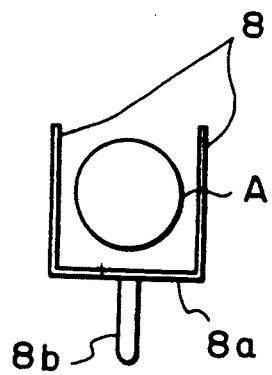
FIG. 3 is a side view of the illumination light path in the first embodiment.
Figure 4:
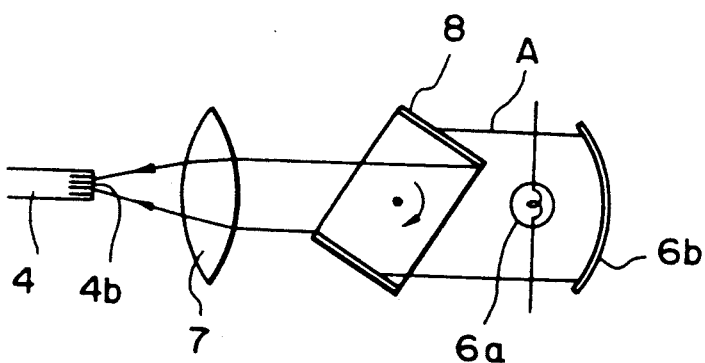
FIG. 4 is a plan view of the illumination light path where plane-parallel plates according to the first embodiment are in a pivoted position.
Figure 5:
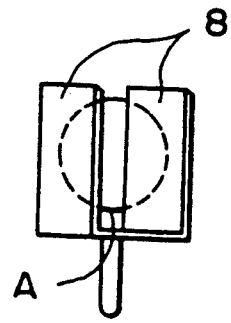
FIG. 5 is a side view of the light path shown in FIG. 4.

In this embodiment, the spacing between the plane-parallel plates 8 is set so as to be greater than the width of the illumination light path A. Accordingly, when the plane-parallel plates 8 are set so as to be parallel with the illumination light path A, as shown in FIGS. 2 and 3, the illumination light reaches the condenser lens 7 without being intercepted at all, so that all of the light enters the incident end 4b of the light guide 4. When the plane-parallel plates 8 are pivoted by means of the motor 9, as shown in FIGS. 4 and 5, two lateral side portions of the illumination light path A are uniformly intercepted by the plane-parallel plates 8. Since the plane-parallel plates 8 are formed from an opaque material, only the light that passes through the area between the plates 8 enters the condenser lens 7. Accordingly, even when the light quantity is decreased by narrowing the cross-sectional area of the illumination light path A, light which evenly includes rays of light passing through the central and peripheral portions of the illumination light path A reaches the condenser lens 7. Therefore, the change in the spectral characteristics is smaller than in the case of the prior art. It should be noted that, since the illumination light is in the form of parallel rays between the light source 6a and the condenser lens 7, the light may be intercepted at any position between them to obtain the same degree of change in the light quantity and it is therefore possible to facilitate the adjustment of the quantity of light by disposing the plane-parallel plates 8 at a position between the light source 6a and the condenser lens 7.

FIGS. 6 to 8 show in combination a second embodiment of the present invention, in which the spacing between plane-parallel plates 28 is set so as to be smaller than the width of the illumination light path A. With this arrangement, when the plane-parallel plates 8 are set in the position for obtaining the maximum light quantity, the illumination light is lost by an amount corresponding to the sum total of the thicknesses of the plane-parallel plates 28, as will be clear from FIG. 6. However, when the light quantity is decreased by narrowing the cross-sectional area of the illumination light path A, light which includes rays of light passing through the central portion B and two lateral side portions C of the illumination light path A reaches the condenser lens 7, as shown in FIGS. 7 and 8. Therefore, the second embodiment has the advantage that the change in the spectral characteristics is smaller than in the case of the first embodiment.

FIGS. 9 to 11 show in combination a third embodiment of the present invention, in which each of the plane-parallel plates 38 is provided with slits 38a which extend parallel with the optical axis of the illumination light. In this embodiment, three slits 38a are cut in each plane-parallel plate 38 in such a manner that the two groups of slits 38a which are respectively provided in the two plates 38 face in the opposite directions to each other. Accordingly, when the plane-parallel plates 38 are pivoted, the illumination light passes through a cross-sectional area which is defined by the area intermediate between the plane-parallel plates 38 and the slits 38a, as shown in FIG. 11. In this case, therefore, even when the light quantity is decreased by narrowing down the cross-sectional area of the illumination light path A, light which evenly includes rays of light passing through the central and peripheral portions of the illumination light path A reaches the condenser lens 7, so that the change in the spectral characteristics is further minimized.

Figure 12:
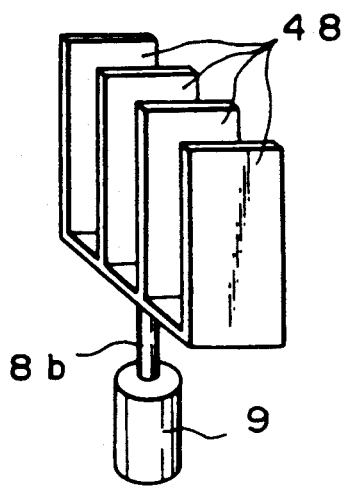
FIG. 12 is a perspective view of plane-parallel plates according to a fourth embodiment of the present invention.
Figure 13:
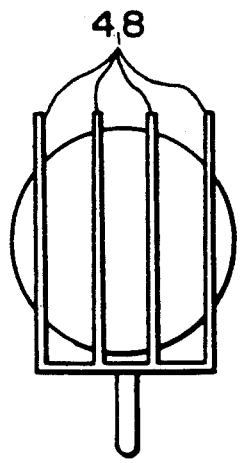
FIG. 13 is a side view of the plane-parallel plates according to the fourth embodiment.
Figure 14:
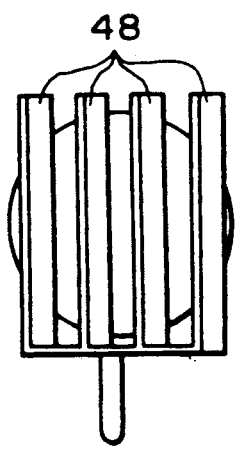
FIG. 14 is a side view of the plane-parallel plates according to the fourth embodiment which are in a pivoted position.

FIGS. 12 to 14 show in combination a fourth embodiment of the present invention, in which four plane-parallel plates 48 are provided. In this case, when the plane-parallel plates 48 are pivoted, light which includes rays of light passing through the central, peripheral and intermediate portions of the illumination light path A reaches the condenser lens 7, as shown in FIG. 14. Accordingly, the change in the spectral characteristics is much smaller than in the case of the first embodiment.

Thus, it is possible to provide any number of plane-parallel plates according to the present invention, provided that the number of plates is two or more. The configuration of the plane-parallel plates employed in the present invention is not necessarily limited to the above-described rectangular shape and the plates may have any desired configuration.

It should be noted that the arrangement of the portions other than the plane-parallel plates in the second to fourth embodiments is the same as that in the first embodiment.

According to the present invention, even when the illumination light quantity is decreased by narrowing the cross-sectional area of the illumination light path, illumination light which evenly includes rays of light passing through the central and peripheral portions of the illumination light path enters the condenser lens and there is therefore a minimized variation in the spectral characteristics between the time when the light quantity is maximized and the time when it is decreased. Accordingly, it is possible to obtain an image having a stable color tone at all times. In addition, there are no variations in the responsiveness of the adjustment of the light quantity and it is therefore possible to obtain an excellent image of which the brightness is stable at all times.

Further, since the present invention enables all of the illumination light to enter the illumination light guide, there is no loss of the light quantity when the maximum light quantity is obtained. In addition, the arrangement of the system is considerably simple.

While the invention has been described by reference to specific embodiments chosen for purpose of illustration, it should be apparent that numerous modifications could be made thereto by those skilled in the art without departing from the basic concept and scope of the invention.

What is claimed is:

1. A light source for an endoscope for supplying illumination to an illumination light guide of said endoscope, said light source system comprising:
   a light source which emits illumination light in an illumination light path having an optical axis;
   a condenser lens for converging the illumination light emitted from said light source on the incident end of said illumination light guide;
   one pair of adjacent plane-parallel plates disposed in the illumination light path at a position between said light source and said condenser lens in such a manner that said plates are in symmetry with each other with respect to the optical axis of said illumination light path, said plane-parallel plates being movable between a fully opened position and at least one light intercepting position, the spacing between the plate of said one pair of adjacent plane-parallel plates being greater than the width of said illumination light path, when said plane-parallel plates are in said fully opened position; and
   means for pivoting said plane-parallel plates so that said one pair of plane-parallel plates intercept the illumination light at both respective sides of said optical axis of said illumination light path, when said plane-parallel plates are in said at least one light intercepting position, illumination light is not intercepted by said plane-parallel plates;
   whereby said plane-parallel plates are pivoted by said pivoting means so as to partially intercept said illumination light path, thereby adjusting the quantity of light entering said illumination light guide.

2. A light source for an endoscope according to claim 1, wherein said illumination light is in the form of parallel rays between said light source and said condenser lens.

3. A light source system for an endoscope according to claim 1, wherein said plane-parallel plates are formed from opaque material.

4. A light source system for an endoscope according to claim 1, wherein each of said plane-parallel plates is substantially rectangular-shaped.

5. A light source system for an endoscope according to claim 1, wherein at least one of the plates of said plane-parallel plates is provided with slits.

6. A light source system for an endoscope according to claim 1, wherein said endoscope includes a solid-state image pickup device which converts an image formed by an objective lens into an electric signal.

7. A light source system for an endoscope according to claim 6, wherein said pivoting means is controlled in response to a signal output from said solid-state image pickup device.

8. A light source system for an endoscope for supplying illumination light to an illumination light guide of said endoscope, said light source system comprising:
   a light source which emits illumination light in an illumination light path having an optical axis;
   a condenser light for converging the illumination light emitted from said light source on the incident end of said illumination light guide;
   at least one pair of plane-parallel plates disposed in the illumination light path at a position between said light source and said condenser lens in such a manner that said plates are in symmetry with each other with respect to the optical axis of said illumination light path, each plate of said at least one pair of plane-parallel plates including at least one slit which extends parallel to said optical axis, each slit being open at an edge of the respective plate, the openings of the slit on each plate facing in the opposite direction to each other; and
   means for pivoting said plane-parallel plates so that said plane-parallel plates intercept the illumination light at both respective sides of said optical axis of said illumination light path;

whereby said plane-parallel plates are pivoted by said pivoting means so as to partially intercept said illumination light path, thereby adjusting the quantity of light entering said illumination light guide.

9. A light source system for an endoscope according to claim 8, including a plurality of slits in each plate of said at least one pair of plane-parallel plates.

10. A light source system for an endoscope according to claim 8, further comprising a connecting plate, wherein said connecting plate includes a single rotating shaft connected thereto, each plate of said at least one pair of plane-parallel plates being integrally formed with each other and said connecting plate, said single rotating shaft extending perpendicular to said optical axis and being parallel with said at least one pair of plane-parallel plates.

11. A light source system for an endoscope for supplying illumination light to an illumination light guide of said endoscope, said light source system comprising:
   a light source which emits illumination light in an illumination light path having an optical axis;
   a condenser lens for converging the illumination light emitted from said light source on the incident end of said illumination light guide;
   at least one pair of plane-parallel plates disposed in the illumination light path at a position between said light source and said condenser lens in such a manner that said plates are in symmetry with each other with respect to the optical axis of said illumination light path, each plate of said at least one pair of plane-parallel plates including at least one slit which extends parallel to said optical axis, each slit being open at an edge of the respective plate, the openings of the slit on each plate facing in the opposite direction to each other; and
   means for pivoting said plane-parallel plates;

whereby said plane-parallel plates are pivoted by said pivoting means so as to partially intercept said illumination light path, thereby adjusting the quantity of light entering said illumination light guide.

12. A light source system for an endoscope according to claim 11, including a plurality of slits in each plate of said at least one pair of plane-parallel plates.

13. A light source for an endoscope for supplying illumination to an illumination light guide of said endoscope, said light source system comprising:
   a light source which emits illumination light in an illumination light path having an optical axis;
   a condenser lens for converging the illumination light emitted from said light source on the incident end of said illumination light guide;
   one pair of plane-parallel plates disposed in the illumination light path at a position between said light source and said condenser lens in such a manner that said plates are in symmetry with each other with respect to the optical axis of said illumination light path, a connecting plate having a single rotating shaft connected thereof, said single rotating shaft extending perpendicular to said optical axis and being parallel with said one pair of plane-parallel plates, wherein the spacing between the plates of said one pair of plane-parallel plates is greater than the width of said illumination light path; and
   means for pivoting said plane-parallel plates with said single rotating shaft;

whereby said plane-parallel plates are pivoted by said pivoting means so as to partially intercept said illumination light path, thereby adjusting the quantity of light entering said illumination light guide.

* * * * *